US008279451B2

(12) United States Patent
Liu et al.

(10) Patent No.: US 8,279,451 B2
(45) Date of Patent: Oct. 2, 2012

(54) PROBING APPARATUS WITH ON-PROBE DEVICE-MAPPING FUNCTION

(75) Inventors: Yong Yu Liu, Hsinchu (TW); Choon Leong Lou, Hsinchu (TW); Lai Peng Chew, Hsinchu (TW)

(73) Assignee: Star Technologies Inc., Hsinchu (TW)

( * ) Notice: Subject to any disclaimer, the term of this patent is extended or adjusted under 35 U.S.C. 154(b) by 307 days.

(21) Appl. No.: 12/796,940

(22) Filed: Jun. 9, 2010

(65) Prior Publication Data

US 2011/0304857 A1 Dec. 15, 2011

(51) Int. Cl.
*G01B 11/24* (2006.01)
*G01B 11/14* (2006.01)

(52) U.S. Cl. ........................................ 356/601; 356/614

(58) Field of Classification Search ........................ None
See application file for complete search history.

(56) References Cited

U.S. PATENT DOCUMENTS

2007/0096763 A1 5/2007 Ehrmann et al.
2009/0236506 A1 9/2009 Dudgeon et al.

OTHER PUBLICATIONS

Korean Office Action dated Sep. 21, 2011 for 10-2010-0081471, which is a corresponding Korean application, that cites US 2007/0096763.

*Primary Examiner* — Gregory J Toatley
*Assistant Examiner* — Amanda Merlino
(74) *Attorney, Agent, or Firm* — WPAT, P.C.; Anthony King (57) ABSTRACT

One aspect of the present disclosure provides a probing apparatus with on-probe device-mapping function. A probing apparatus according to this aspect of the present disclosure comprises a housing, at least one probe stage positioned on the housing and configured to retain at least one probe, a device holder positioned in the housing and configured to receive at least one semiconductor device under test, and an inspection module having a predetermined field of view configured to capture an image showing at least the semiconductor device, wherein the probe stage includes a driving unit configured to move the probe out of focus of the inspection module in a mapping phase while keeping the device under test in the field of view of the optical inspection module.

33 Claims, 7 Drawing Sheets

PROBING APPARATUS WITH ON-PROBE DEVICE-MAPPING FUNCTION

BACKGROUND OF THE DISCLOSURE (A) Field of the Disclosure

The present disclosure relates to a probing apparatus with on-probe device-mapping function, and more particularly, to a probing apparatus with on-probe device-mapping function implemented by moving the probe out of focus of the optical inspection module while keeping the device under test in the field of view of the optical inspection module.

(B) Description of the Related Art

Optical imaging systems are used for inspection of semiconductor devices such as light-emitting diodes (LED) and integrated circuit devices. In a typical semiconductor device test process, the wafer is first placed on blue tape before being cut into individual semiconductor devices where each semiconductor device is isolated from others on the wafer. The blue tape with the semiconductor devices on it is then mounted onto a circular rim for testing. The imaging system provides the means for navigating the semiconductor devices on the rim as well as the probing process. As the semiconductor device positions are slightly distorted during the cutting from wafer and transfer to the rim, and in view of the large number of semiconductor devices to be inspected and probed on the wafer, device mapping is usually performed prior to probing. The mapping collects and records the information of each of the semiconductor devices including its position, presence or absence, ink marking, etc. In a typical device test cycle, a group of semiconductor devices is positioned under the field of view (FOV) of the imaging system. A semiconductor device pattern is then learned by the imaging system and will be used as master pattern for the search of other semiconductor devices within the FOV using the commonly used pattern-matching technique.

However, because the presence of the probes above the semiconductor devices can cause blocking of the image and incomplete mapping of the semiconductor devices, most inspection apparatuses use a second imaging system when performing the device mapping. The second imaging system is mounted some distance away from the first imaging system and the semiconductor device positioning stage needs to move the semiconductor devices to the second imaging system for the device-mapping process. After the device mapping is completed, the semiconductor devices are moved back to the first imaging system for probing. The imaging system's optical centers for probing and mapping need to be precisely aligned in order to avoid incorrect positioning of the semiconductor devices.

The inspection apparatus described above, however, has the disadvantage of requiring two imaging systems, as well as the disadvantage of requiring precise position alignment of the two optical centers. Further disadvantages include the time requirement for the semiconductor device positioning stage to move from one imaging system to the other and the extra travel range required to move the semiconductor device positioning stage between the two imaging systems.

U.S. patent publication number US 2009/0236506 A1 discloses an On-wafer test system and method for light-emitting devices, such as light-emitting diodes (LEDs). The system comprises a wafer including an LED die designed to emit light and a light-collection component configured to collect substantially all of the emitted light and to scatter the emitted light to produce a distribution of scattered light. The system further comprises a detector associated with the light-collection component and designed to detect a portion of the scattered light.

SUMMARY OF THE DISCLOSURE

One aspect of the present disclosure provides a probing apparatus with on-probe device-mapping function implemented by moving the probe out of focus of the optical inspection module while keeping the device under test in the field of view of the optical inspection module. A probing apparatus according to this aspect of the present disclosure comprises a housing, at least one probe stage positioned on the housing and configured to retain at least one probe, a device holder positioned in the housing and configured to receive at least one semiconductor device under test, and an inspection module having a predetermined field of view configured to capture an image showing at least the semiconductor device, wherein the probe stage includes a driving unit configured to move the probe out of focus of the inspection module in a mapping phase while keeping the device under test in the field of view of the optical inspection module.

Another aspect of the present disclosure provides a probing apparatus with on-probe device-mapping function implemented by moving the probe out of focus of the optical inspection module while keeping the device under test in the field of view of the optical inspection module. A probing apparatus according to this aspect of the present disclosure comprises a housing, at least one probe stage positioned on the housing and configured to retain at least one probe, a device holder positioned in the housing and configured to receive at least one semiconductor device under test, a device stage configured to support the device holder, an inspection module having a predetermined field of view configured to capture an image showing at least the semiconductor device, and an inspection stage configured to support the inspection module. In one embodiment of the present disclosure, the device stage includes a first driving unit configured to move the device holder along a first axis, the inspection stage includes a second driving unit configured to move the inspection module along the first axis, and the first driving unit and the second driving unit are enabled in a mapping phase to move along the first axis such that the probe is out of focus of the inspection module while the device under test is in the field of view of the optical inspection module.

The foregoing has outlined rather broadly the features and technical advantages of the present disclosure in order that the detailed description of the disclosure that follows may be better understood. Additional features and advantages of the disclosure will be described hereinafter, and form the subject of the claims of the disclosure. It should be appreciated by those skilled in the art that the conception and specific embodiment disclosed may be readily utilized as a basis for modifying or designing other structures or processes for carrying out the same purposes as those of the present disclosure. It should also be realized by those skilled in the art that such equivalent constructions do not depart from the spirit and scope of the disclosure as set forth in the appended claims.

BRIEF DESCRIPTION OF THE DRAWINGS

The objectives and advantages of the present disclosure will become apparent upon reading the following description and upon reference to the accompanying drawings in which.

DETAILED DESCRIPTION OF THE DISCLOSURE

Figure 1:
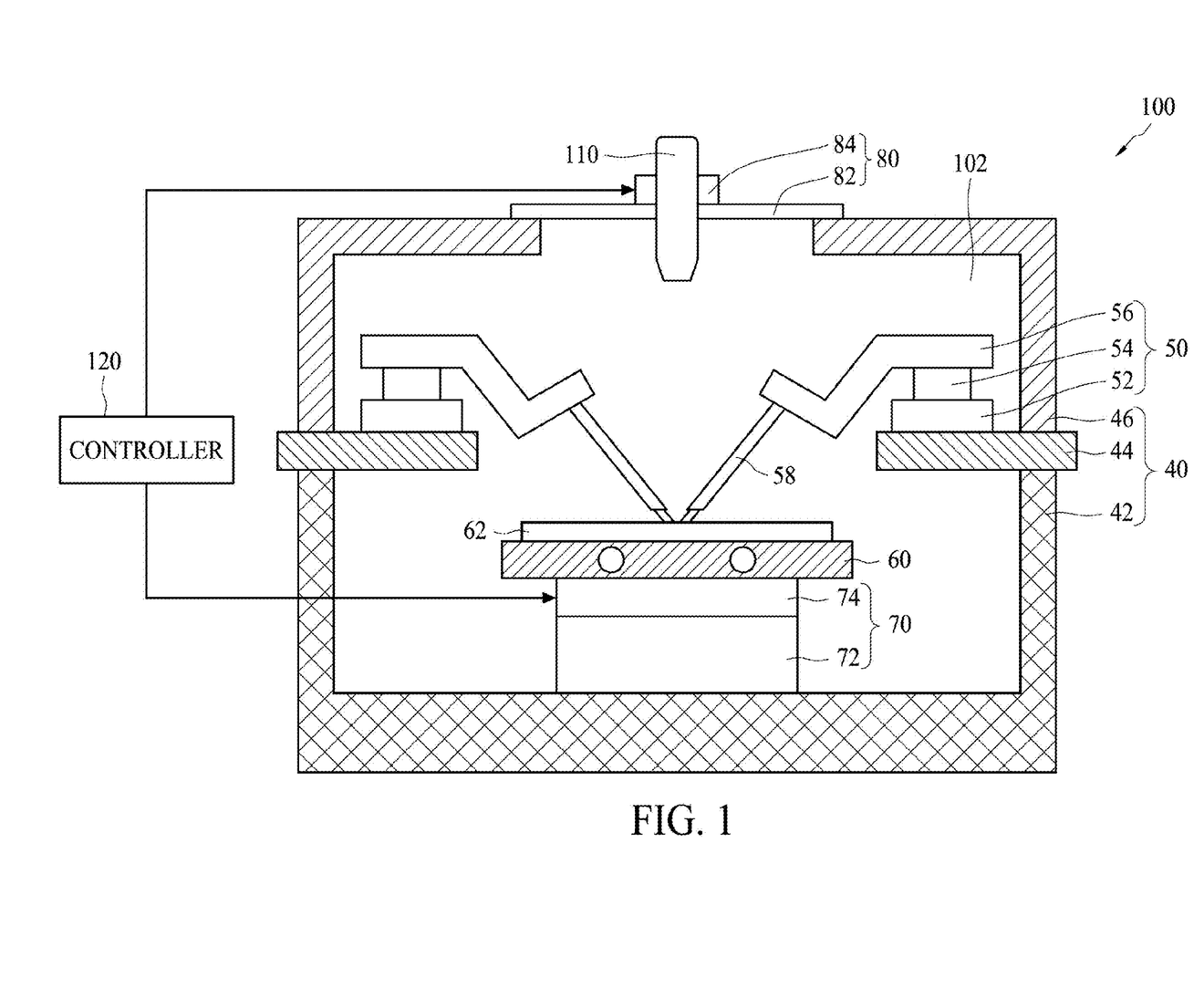
FIG. 1 illustrates a probing apparatus according to one embodiment of the present disclosure.

FIG. 1 illustrates a probing apparatus 100 according to one embodiment of the present disclosure. The probing apparatus 100 comprises a housing 40, at least one probe stage 50 positioned in the housing 40 and configured to retain at least one probe 58, a device holder 60 positioned in the housing and configured to receive at least one semiconductor device 62 under test, and an inspection module 110 having a predetermined field of view configured to capture an image showing at least the semiconductor device 62. In one embodiment of the present disclosure, the housing 40 includes a body 42, a platen 44 positioned on the body 42 and a cover 46 configured to form a testing chamber 102 with the probe stage 50 and the device holder 60 positioned inside the testing chamber 102, wherein the probe stage 50 is positioned on the platen 44.

Figure 2:
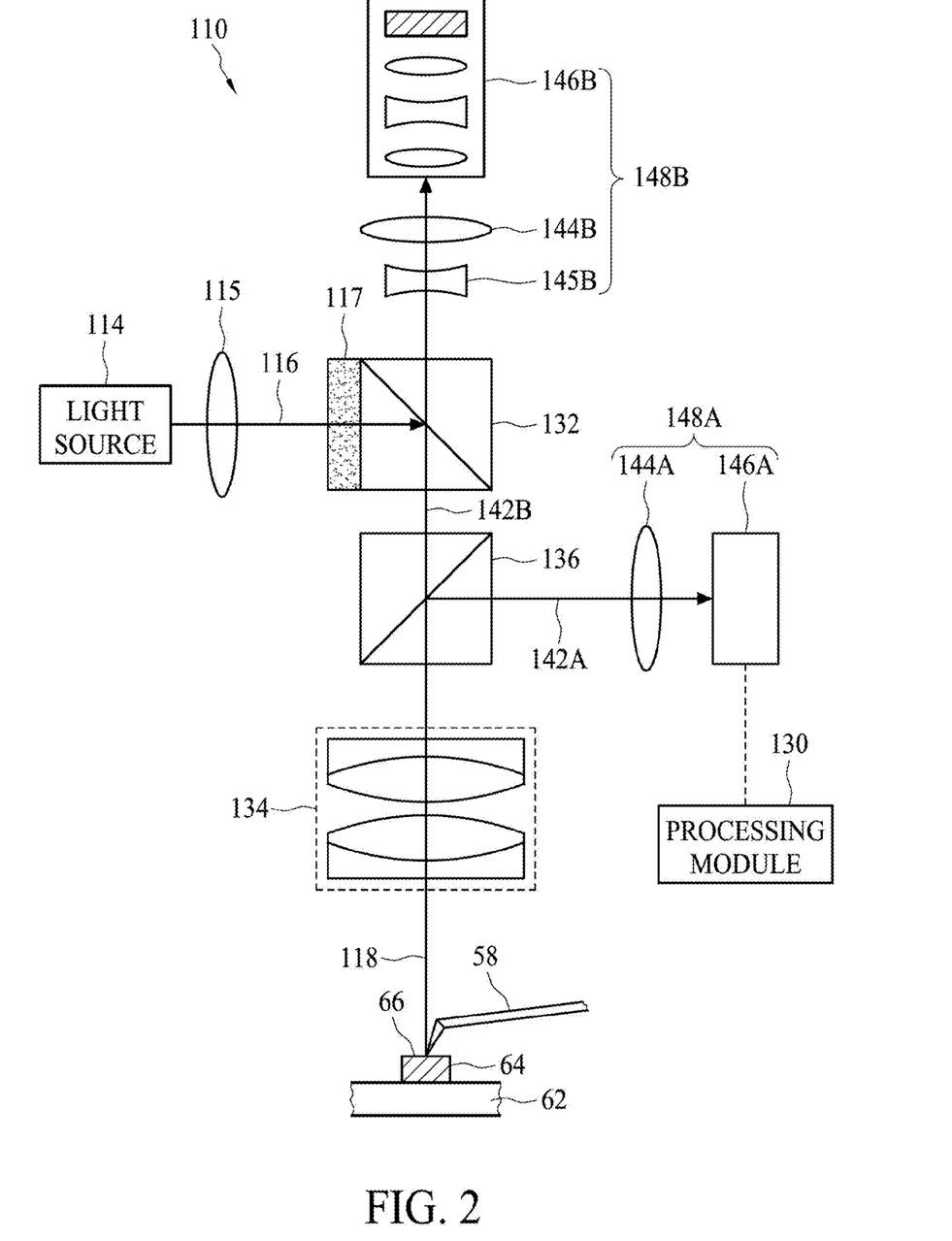
FIG. 2 illustrates an inspection module according to one embodiment of the present disclosure.
Figure 3:
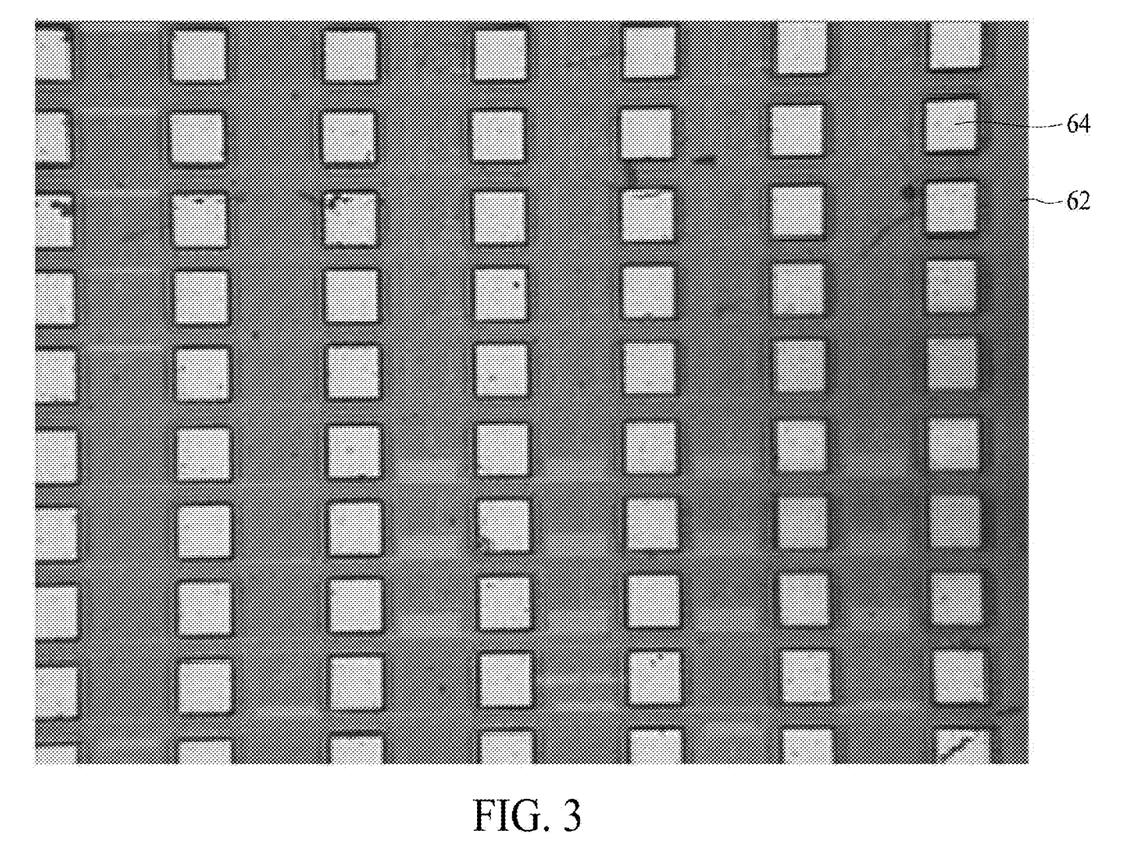
FIG. 3 and FIG. 4 show the images captured by the inspection module according to one embodiment of the present disclosure.
Figure 4:
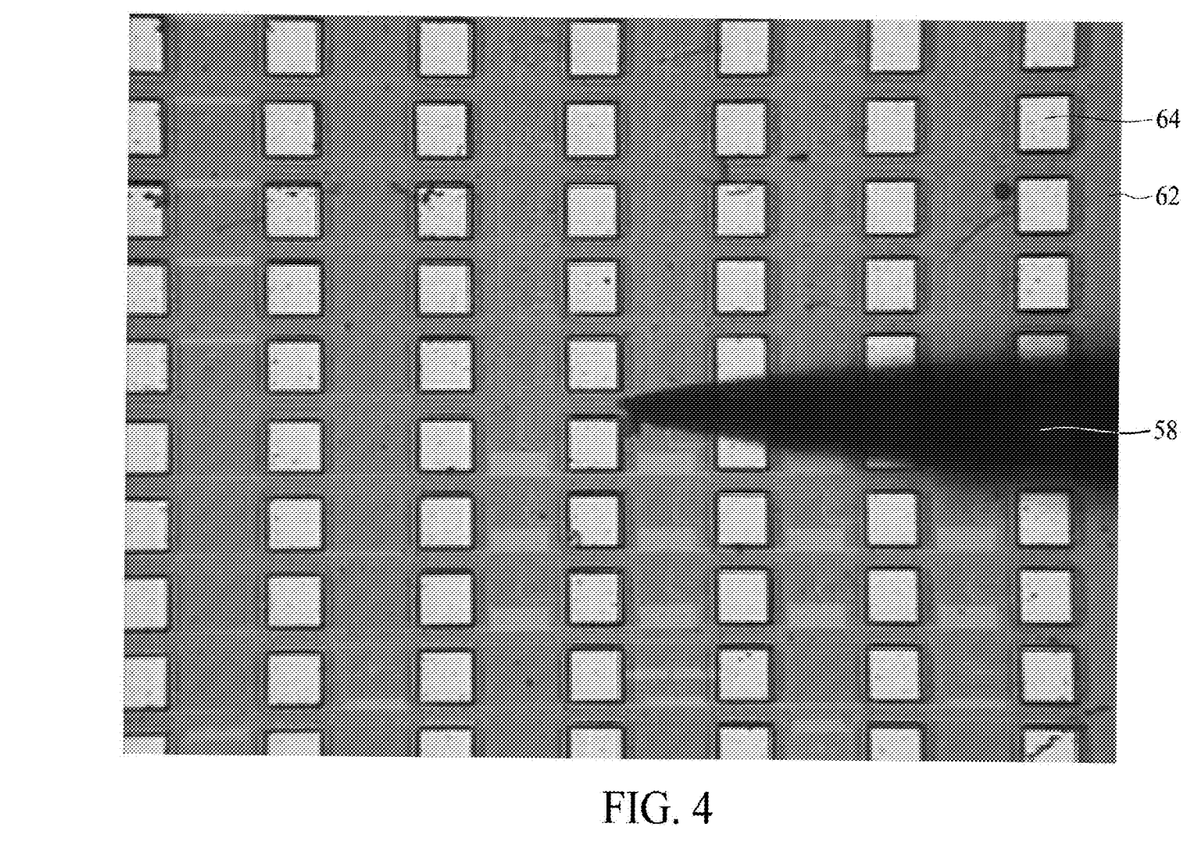

FIG. 2 illustrates an inspection module 110 according to one embodiment of the present disclosure, and FIG. 3 and FIG. 4 show the images captured by the inspection module 110. The inspection module 110 comprises a first beam splitter 132 configured to direct an illumination light 116 to an object plane 66, an objective lens 134 configured to collect the reflected light 118 from the object plane 66, and a second beam splitter 136 configured to split the reflected light 118 into a first optical path 142A and a second optical path 142B. In one embodiment of the present disclosure, the inspection module 110 includes a positive lens 115 such as a condenser lens positioned between the first splitter 132 and a light surface 114 emitting the illumination light 116, and a diffuser 117 disposed on a surface of the first splitter 132 receiving the illumination light 116.

In one embodiment of the present disclosure, the inspection module 110 further comprises a first imaging module 148A positioned on the first optical path 142A and a second imaging module 148B positioned on the second optical path 142B. In one embodiment of the present disclosure, the first imaging module 148A includes a first close up lens 144A configured to render a first object image (FIG. 3) to a first imaging device 146A such as charge-coupled devices (CCD) with high image resolution capabilities, and the second imaging module 148B includes a second close up lens 144B and a negative lens 145B configured to render a second object image (FIG. 4) to a second imaging device 146B such as CCD with zooming capabilities.

Referring back to FIG. 1, the probe stage 50 includes a driving unit 52 configured to move the probe 58 along the X-axis and the Y-axis, a driving unit 54 configured to move the probe 58 along the Z-axis, and a carrier 56 configured to retain the probe 58. In an alignment process, the probe 58 is positioned by using the probe stage 50 to move into position allowing contact with a contact 64 of the semiconductor device 62 on the device holder 60, wherein the operator can use the second imaging module 148B to observe the second object image (FIG. 4) showing the relative position of the probe 58 and the contact 64 of the semiconductor device 62, and the zooming capability of the second imaging module 148B can be used to observe in detail the relative position of the probe 58 and the contact 64 of the semiconductor device 62.

Once the probe 58 is aligned and contacted with the contact 64 of the semiconductor device 62, the driving unit 54 is enabled to move the probe 58 along the Z-axis such that the probe 58 is not in focus of the inspection module 110 and appears to be nearly transparent to the inspection module 110 in the mapping phase. In one embodiment of the present disclosure, the probing apparatus 100 is configured to move the probe 58 preferably out of the depth of focus (DOF) of the inspection module 110 in the mapping phase while keeping the semiconductor device 62 in the DOF of the inspection module 110 by enabling the driving unit 54 to move the probe 58 toward the inspection module 110 along the Z-axis.

Consequently, the operator can use the first imaging module 148A to observe the first object image (FIG. 3) substantially without the probe 58. Subsequently, a contact 64 of the semiconductor device 62 will be selected as a teach pattern, and a processing module 130 coupled to the inspection module 110 is enabled to identify all the contact positions of the semiconductor device 62. The processing module 130, implemented by either hardware or software, learns the teach pattern, which is then used for the search for other identical patterns during the mapping process using pattern matching technique. Because the probe 58 appears transparent, all identical contact patterns will be identified by the pattern search and thus the device mapping process can be performed even though the probe 58 is equipped on the probing apparatus, i.e., on-probe device-mapping is achieved.

Referring back to FIG. 1, the probing apparatus 100 further comprises a device stage 70 configured to support the device holder 60 and an inspection stage 80 configured to support the inspection module 110. In one embodiment of the present disclosure, the device stage 70 includes a driving unit 72 configured to move the device holder 60 along the X-axis and the Y-axis and a driving unit 74 configured to move the device holder 60 along the Z-axis; the inspection stage 80 includes a driving unit 82 configured to move the inspection module 110 along the X-axis and the Y-axis and a driving unit 84 configured to move the inspection module 110 along the Z-axis. In one embodiment of the present disclosure, the probing apparatus 100 further comprises a controller 120 configured to control the driving unit 74 and the driving unit 84 in a mapping phase to move in a synchronous manner along the Z-axis such that the probe 58 is out of focus (preferably out of the DOF) of the inspection module 110 while the semiconductor device 62 under test is still in the DOF of the optical inspection module 110.

In an alignment process, the probe 58 is positioned by using the probe stage 50 to move into contact with a contact 64 of the semiconductor device 62 on the device holder 60, wherein the operator can use the second imaging module 148B to observe the second object image (FIG. 4) showing the relative position of the probe 58 and the contact 64 of the semiconductor device 62. Once the probe 58 is aligned and contacted with the contact 64 of the semiconductor device 62, both the driving unit 74 of the device stage 70 and the driving unit 84 of the inspection stage 80 are enabled to synchronously move the semiconductor device 62 and the inspection module 110 along the Z-axis such that the probe 58 is not in focus (preferably out of the DOF) of the inspection module 110 and appears to be nearly transparent to the inspection module 110 in the mapping phase.

Consequently, the operator can use the first imaging module 148A to observe the first object image (FIG. 3) substantially without the probe 58. Subsequently, a contact 64 of the semiconductor device 62 is selected as a teach pattern, and a processing module 130 coupled to the inspection module 110 is enabled to identify the contact position of the semiconductor device 62. The processing module 130, implemented by either hardware or software, learns the teach pattern, which is then used for the search of other identical patterns during the mapping process using pattern matching technique. Because the probe 58 appears transparent, all identical contact patterns will be identified by the pattern search and thus the device mapping process can be performed even though the probe 58 is equipped on the probing apparatus, i.e., on-probe device-mapping is achieved.

Figure 5:
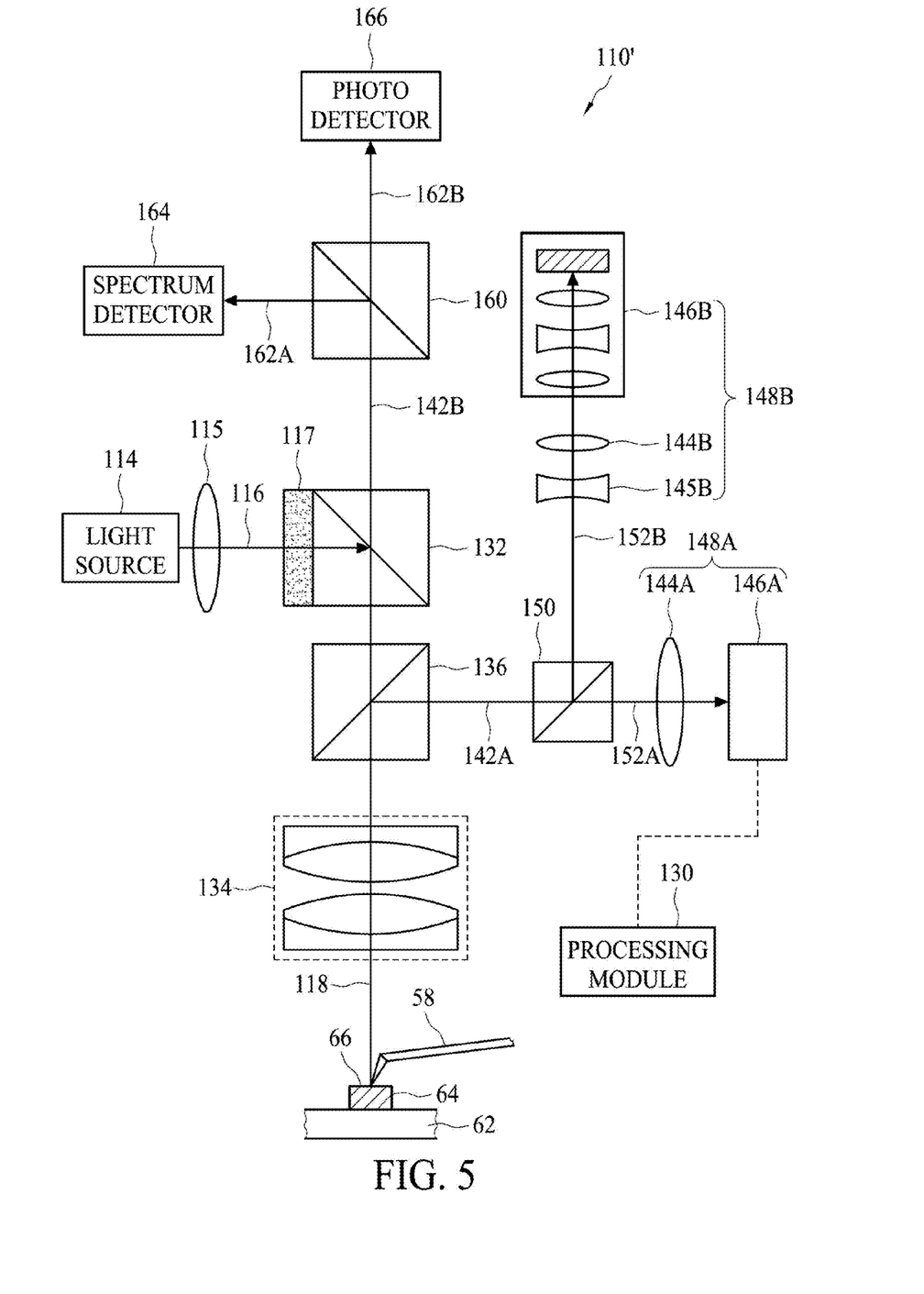
FIG. 5 illustrates an inspection module according to another embodiment of the present disclosure.

FIG. 5 illustrates an inspection module 110' according to another embodiment of the present disclosure. The inspection module 110' comprises a first beam splitter 132 configured to direct an illumination light 116 to an object plane 66, an objective lens 134 configured to collect the reflected light 118 from the object plane 66, and a second beam splitter 136 configured to split the reflected light 118 into a first optical path 142A and a second optical path 142B. In one embodiment of the present disclosure, the inspection module 110' includes a positive lens 115 such as a condenser lens positioned between the first splitter 132 and a light surface 114 emitting the illumination light 116, and a diffuser 117 disposed on a surface of the first splitter 132 receiving the illumination light 116.

In one embodiment of the present disclosure, the inspection module 110' further comprises a third beam splitter 150 positioned on the first optical path 142A and a fourth beam splitter 160 positioned on the second optical path 142B. The third beam splitter 150 is configured to split the reflected light 118 into at least a third optical path 152A and a fourth optical path 152B, and the fourth beam splitter 160 is configured to split the reflected light 118 into at least a fifth optical path 162A and a sixth optical path 162B. In one embodiment of the present disclosure, the inspection module 110' further comprises a first imaging module 148A positioned on the third optical path 152A, and a second imaging module 148B positioned on the fourth optical path 152B.

In one embodiment of the present disclosure, the first imaging module 148A includes a first close up lens 144A configured to render a first object image (FIG. 3) to a first imaging device 146A such as CCD with high image resolution capabilities, and the second imaging module 148B includes a second close up lens 144B and a negative lens 145B configured to render a second object image (FIG. 4) to a second imaging device 146B such as CCD with zooming capabilities. In one embodiment of the present disclosure, the inspection module 110' further comprises a photo detector 164 positioned on the fifth optical path 162A and a spectrum detector 166 positioned on the sixth optical path 162B, particularly for probing the optical properties of optoelectronic devices such as the light-emitting devices.

Figure 6:
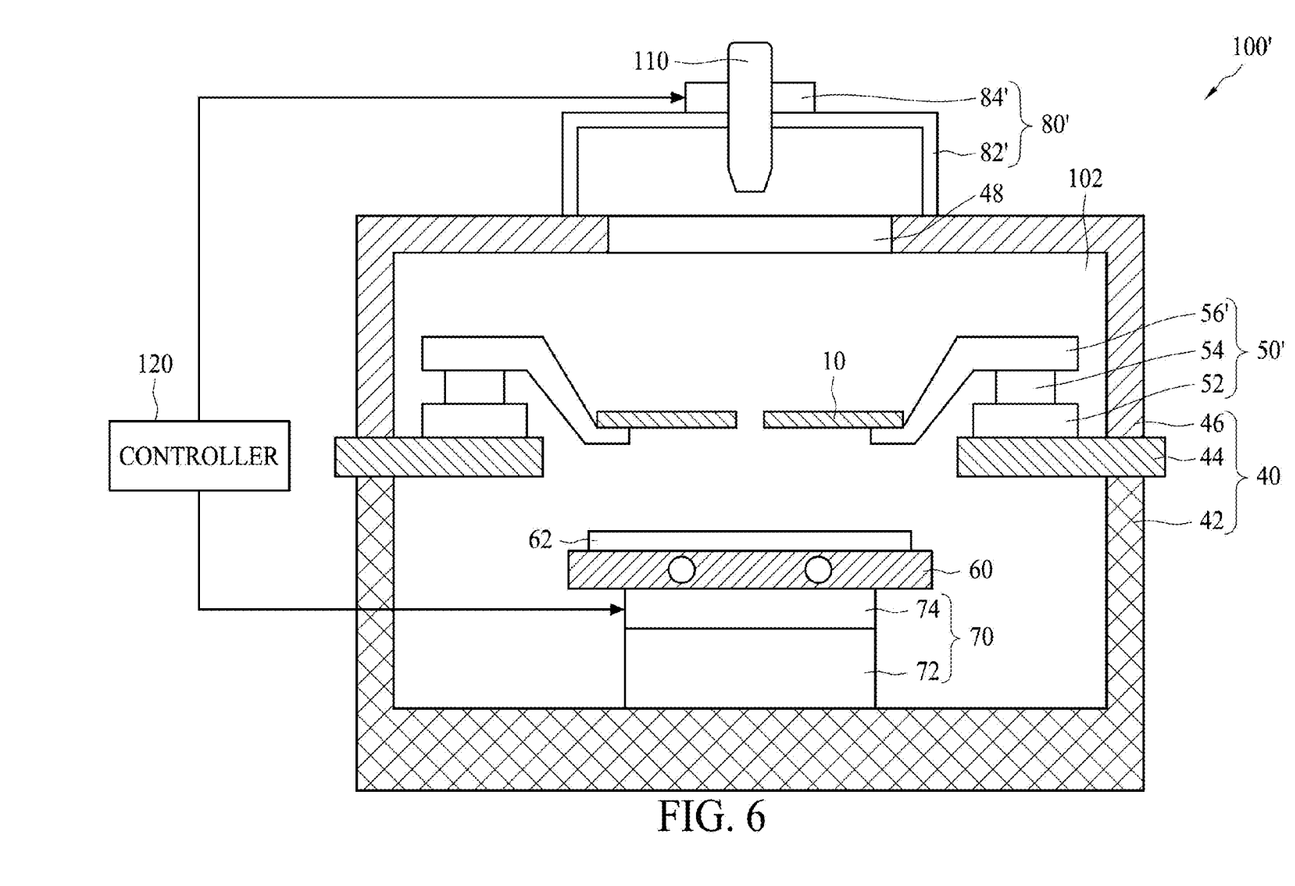
FIG. 6 illustrates a probing apparatus according to another embodiment of the present disclosure.
Figure 7:
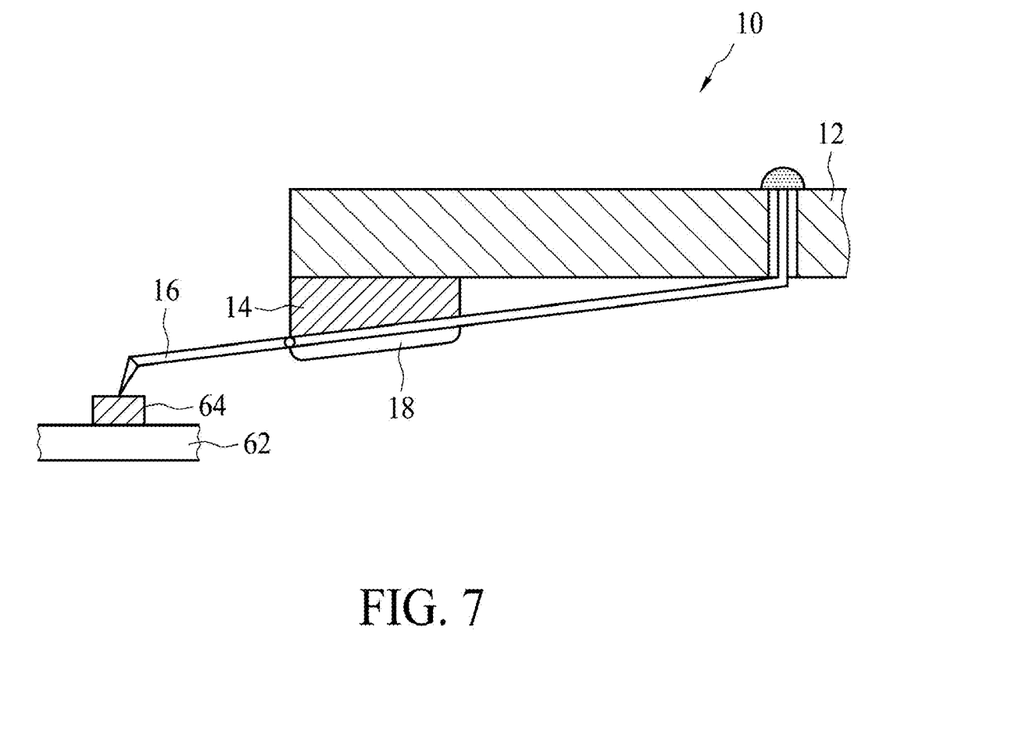
FIG. 7 illustrates the probe card according to one embodiment of the present disclosure.

FIG. 6 illustrates a probing apparatus 100' according to another embodiment of the present disclosure. The probing apparatus 100' comprises a housing 40, at least one probe stage 50' positioned on the housing 40 and configured to retain at least one probe card 10, a device holder 60 positioned in the housing 40 and configured to receive at least one semiconductor device 62 under test, and an inspection module 110 having a predetermined field of view configured to capture an image showing at least the semiconductor device 62. In one embodiment of the present disclosure, the housing 40 includes a body 42, a platen 44 on the body 42 and a cover 46 configured to form a testing chamber 102 with the probe stage 50 and the device holder 60 positioned inside the testing chamber 102, wherein the probe stage 50' is positioned on the platen 44. FIG. 7 illustrates the probe card 10 according to one embodiment of the present disclosure. The probe card 10 includes a substrate 12, a supporter 14 positioned on the substrate 12, a plurality of probes 16 positioned on the supporter 14, and a conductive through hole 20 connecting the probe 16 and a conductive wire 26. The probe 16 is fixed on the supporter 14 by epoxy resin 24. The cover 46 has a transparent window 48 for observing the relative position of the semiconductor device 62 and the probe 16. In one embodiment of the present disclosure, the inspection module 110 is configured to capture an alignment image of the semiconductor device 62 and the probe 16 through the transparent window 48 of the cover 46.

In one embodiment of the present disclosure, the probe stage 50' includes a driving unit 52 configured to move the probe card 10 along the X-axis and the Y-axis, a driving unit 54 configured to move the probe card 10 along the Z-axis, and a carrier 56' configured to retain the probe card 10. In one embodiment of the present disclosure, the probing apparatus 100' is configured to move the probe 16 of the probe card 10 out of focus (preferably out of the DOF) of the inspection module 110 in the mapping phase while keeping the semiconductor device 62 in the DOF of the inspection module 110 by enabling the driving unit 54 to move the probe 16 toward the inspection module 110 along the Z-axis. In another embodiment of the present disclosure, the probing apparatus 100' further comprises a controller 120 configured to control the driving unit 74 and the driving unit 84' in the mapping phase to move in a synchronous manner along the Z-axis such that the probe 16 of the probe card 10 is out of focus (preferably out of the DOF) of the inspection module 110 while the semiconductor device 62 under test is still in the DOF of the optical inspection module 110.

Although the present disclosure and its advantages have been described in detail, it should be understood that various changes, substitutions and alterations can be made herein without departing from the spirit and scope of the disclosure as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:
1. A probing apparatus, comprising:
a housing;
at least one probe stage positioned in the housing and configured to retain at least one probe;
a device holder positioned in the housing and configured to receive at least one semiconductor device under test; and an inspection module having a predetermined field of view configured to capture an image showing at least the semiconductor device;

wherein the probe stage includes a driving unit configured to move the probe out of focus of the inspection module in a mapping phase.

2. The probing apparatus of claim 1, wherein the inspection module comprises:
a first beam splitter configured to direct an illumination light to an object plane;
an objective lens configured to collect a reflected light from the object plane; and
a second beam splitter configured to split the reflected light into at least a first optical path and a second optical path.

3. The probing apparatus of claim 2, wherein the inspection module further comprises:
a first imaging module positioned on the first optical path, the first imaging module including a first close up lens configured to render a first object image to a first imaging device; and
a second imaging module positioned on the second optical path, the second imaging module including a second close up lens and a negative lens configured to render a second object image to a second imaging device with zooming capabilities.

4. The probing apparatus of claim 2, wherein the inspection module further comprises:
a third beam splitter positioned on the first optical path and configured to split the reflected light into at least a third optical path and a fourth optical path; and
a fourth beam splitter positioned on the second optical path and configured to split the reflected light into at least a fifth optical path and a sixth optical path.

5. The probing apparatus of claim 4, wherein the inspection module further comprises:
a first imaging module positioned on the first optical path, the first imaging module including a first close up lens configured to render a first object image to a first imaging device; and
a second imaging module positioned on the second optical path, the second imaging module including a second close up lens and a negative lens configured to render a second object image to a second imaging device with zooming capabilities.

6. The probing apparatus of claim 4, wherein the inspection module further comprises a photo detector positioned on the fifth optical path and a spectrum detector positioned on the sixth optical path.

7. The probing apparatus of claim 1, wherein the probe stage comprises a carrier configured to retain the probe.

8. The probing apparatus of claim 1, wherein the probe stage comprises a carrier configured to retain a probing card including the probe.

9. The probing apparatus of claim 1, wherein the housing comprises a cover configured to form an isolation chamber with the probe stage and the device holder positioned therein.

10. The probing apparatus of claim 9, wherein the cover comprising a transparent window and the inspection module is configured to capture the image through the transparent window.

11. The probing apparatus of claim 1, wherein the housing comprises a platen, and the probe stage is positioned on the platen.

12. The probing apparatus of claim 1, wherein the driving unit is configured to move the probe out of focus of the inspection module along the Z-axis.

13. The probing apparatus of claim 12, wherein the driving unit is configured to move the probe toward the inspection module.

14. The probing apparatus of claim 1, further comprising a processing module coupled to the inspection module and configured to identify at least a contact position of the semiconductor device.

15. The probing apparatus of claim 2, further comprising a positive lens positioned between the first splitter and a light surface for emitting the illumination light, and a diffuser disposed on a surface of the first splitter receiving the illumination light.

16. The probing apparatus of claim 1, wherein the driving unit is configured to move the probe out of the depth of focus of the inspection module in the mapping phase.

17. A probing apparatus, comprising:
a housing;
at least one probe stage positioned on the housing and configured to retain at least one probe;
a device holder positioned in the housing and configured to receive at least one semiconductor device under test;
a device stage configured to support the device holder, the device stage including a first driving unit configured to move the device holder along a first axis;
an inspection module having a predetermined field of view configured to capture an image showing at least the semiconductor device;
an inspection stage configured to support the inspection module and including a second driving unit configured to move the inspection module along the first axis;
wherein the first driving unit and the second driving unit are enabled in a mapping phase to move along the first axis such that the probe is out of focus of the inspection module.

18. The probing apparatus of claim 17, further comprising a controller configured to control the first driving unit and the second driving unit to move in a synchronous manner.

19. The probing apparatus of claim 17, wherein the first driving unit is configured to move the device holder along the Z-axis.

20. The probing apparatus of claim 17, wherein the second driving unit is configured to move the inspection module along the Z-axis.

21. The probing apparatus of claim 17, wherein the inspection module comprises:
a first beam splitter configured to direct an illumination light to an object plane;
an objective lens configured to collect a reflected light from the object plane; and
a second beam splitter configured to split the reflected light into at least a first optical path and a second optical path.

22. The probing apparatus of claim 21, wherein the inspection module further comprises:
a first imaging module positioned on the first optical path, the first imaging module including a first close up lens configured to render a first object image to a first imaging device; and
a second imaging module positioned on the second optical path, the second imaging module including a second close up lens and a negative lens configured to render a second object image to a second imaging device with zooming capabilities.

23. The probing apparatus of claim 21, wherein the inspection module further comprises:
a third beam splitter positioned on the first optical path and configured to split the reflected light into at least a third optical path and a fourth optical path; and a fourth beam splitter positioned on the second optical path and configured to split the reflected light into at least a fifth optical path and a sixth optical path.

24. The probing apparatus of claim 23, wherein the inspection module further comprises:

a first imaging module positioned on the first optical path, the first imaging module including a first close up lens configured to render a first object image to a first imaging device; and a second imaging module positioned on the second optical path, the second imaging module including a second close up lens and a negative lens configured to render a second object image to a second imaging device with zooming capabilities.

25. The probing apparatus of claim 23, wherein the inspection module further comprises a photo detector positioned on the fifth optical path and a spectrum detector positioned on the sixth optical path.

26. The probing apparatus of claim 17, wherein the probe stage comprises a carrier configured to retain the probe.

27. The probing apparatus of claim 17, wherein the probe stage comprises a carrier configured to retain a probing card including the probe.

28. The probing apparatus of claim 17, wherein the housing comprises a cover configured to form an isolation chamber with the probe stage and the device holder positioned therein.

29. The probing apparatus of claim 28, wherein the cover comprising a transparent window and the inspection module is configured to capture the image through the transparent window.

30. The probing apparatus of claim 17, wherein the housing comprises a platen, and the probe stage is positioned on the platen.

31. The probing apparatus of claim 17, further comprising a processing module coupled to the inspection module and configured to identify at least a contact position of the semiconductor device.

32. The probing apparatus of claim 21, further comprising a positive lens positioned between the first splitter and a light surface for emitting the illumination light, and a diffuser disposed on a surface of the first splitter receiving the illumination light.

33. The probing apparatus of claim 17, wherein the first driving unit and the second driving unit are enabled in the mapping phase to move along the first axis such that the probe is out of the depth of focus of the inspection module.

* * * * *